(12) United States Patent
Bhaduri et al.

(10) Patent No.: US 10,342,893 B2
(45) Date of Patent: Jul. 9, 2019

(54) INJECTABLE, BIODEGRADABLE BONE CEMENTS AND METHODS OF MAKING AND USING SAME

(71) Applicant: The University of Toledo, Toledo, OH (US)

(72) Inventors: Sarit B. Bhaduri, Holland, OH (US); Huan Zhou, Toledo, OH (US); Anand K. Agarwal, Ottawa Hills, OH (US); Vijay K. Goel, Holland, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 14/375,927

(22) PCT Filed: Jan. 31, 2013

(86) PCT No.: PCT/US2013/024040
§ 371 (c)(1),
(2) Date: Jul. 31, 2014

(87) PCT Pub. No.: WO2013/116457
PCT Pub. Date: Aug. 8, 2013

(65) Prior Publication Data
US 2015/0005392 A1 Jan. 1, 2015

Related U.S. Application Data

(60) Provisional application No. 61/593,094, filed on Jan. 31, 2012, provisional application No. 61/697,059, filed on Sep. 5, 2012.

(51) Int. Cl.
| | | |
|---|---|---|
| *A61L 24/00* | (2006.01) | |
| *A61C 5/62* | (2017.01) | |
| *A61L 27/32* | (2006.01) | |
| *A61L 24/08* | (2006.01) | |
| *A61B 17/88* | (2006.01) | |
| *C23C 30/00* | (2006.01) | |
| *A61K 6/097* | (2006.01) | |
| *A61K 6/00* | (2006.01) | |
| *A61L 24/02* | (2006.01) | |
| *A61K 6/06* | (2006.01) | |
| *A61C 5/06* | (2006.01) | |

(52) U.S. Cl.
CPC ...... *A61L 24/0063* (2013.01); *A61B 17/8805* (2013.01); *A61C 5/062* (2013.01); *A61C 5/62* (2017.02); *A61K 6/0082* (2013.01); *A61K 6/0643* (2013.01); *A61K 6/097* (2013.01); *A61L 24/0015* (2013.01); *A61L 24/0021* (2013.01); *A61L 24/0036* (2013.01); *A61L 24/0042* (2013.01); *A61L 24/0084* (2013.01); *A61L 24/02* (2013.01); *A61L 24/08* (2013.01); *A61L 27/32* (2013.01); *C23C 30/005* (2013.01); *A61L 2400/06* (2013.01); *A61L 2420/04* (2013.01); *A61L 2430/02* (2013.01); *A61L 2430/12* (2013.01)

(58) Field of Classification Search
None
See application file for complete search history.

(56) References Cited

U.S. PATENT DOCUMENTS

| | | | |
|---|---|---|---|
| 8,506,985 B2 | 8/2013 | Garcia De Castro Andrews et al. | |
| 2002/0114753 A1 | 8/2002 | Green et al. | |
| 2005/0271742 A1 | 12/2005 | Chern Lin et al. | |
| 2008/0206716 A1 | 8/2008 | Asgary | |
| 2010/0173846 A1 | 7/2010 | Zimmermann | |
| 2012/0191214 A1 | 7/2012 | Nies | |
| 2015/0005392 A1 | 1/2015 | Bhaduri et al. | |

FOREIGN PATENT DOCUMENTS

| | | |
|---|---|---|
| CA | 2325740 A1 | 10/1999 |
| CN | 1333196 A | 1/2002 |
| CN | 1569256 A | 1/2005 |
| CN | 102316911 A | 1/2012 |
| EP | 1172076 A2 | 1/2002 |
| JP | 2002509766 A | 4/2002 |
| JP | 2010529091 A | 8/2010 |
| JP | 2015505511 A | 2/2015 |

(Continued)

OTHER PUBLICATIONS

"The Physical Properties of Magnesium Oxide," available from http://livestrong.com/article/500557-the-physical-properties-ofmagnesium-oxide/, as accessed Feb. 24, 2017.*
Klammert, U., et al., Acta Biomaterialia 7: 3469-3475 (available online May 25, 2011).*
Klammert, U., Acta Biomaterialia 6: 1529-1535 (available online Nov. 1, 2009).*
Desai et al., "A Self-Setting, Monetite (CaHPO4) Cement for Skeletal Repair", Advances in Bioceramics and Biocomposites II, 2007, pp. 61-69.
Tamimi et al., "Dicalcium Phosphate Cements: Brushite and Monetite", Acta Biomaterialia, 2012, vol. 8, pp. 474-487.
Touny et al., "Hydrolysis of monetite/chitosan composites in α-MEM and SBF solutions", The Journal of Materials Science: Materials in Medicine, 2011, vol. 22, pp. 1101-1109.
PCT International Search Report and the Written Opinion, Application No. PCT/US2013/024040 filed Jan. 31, 2013, dated Apr. 4, 2013.

(Continued)

*Primary Examiner* — David J Blanchard
*Assistant Examiner* — Daniel F. Coughlin
(74) *Attorney, Agent, or Firm* — MacMillan, Sobanski & Todd, LLC

(57) ABSTRACT

Compositions of, methods of making, and methods of using alkaline earth phosphate bone cements are disclosed. A bone cement composition includes a powder comprising a basic source of calcium, magnesium, or strontium, a setting solution comprising H3PO4 and a buffer, and a biocompatible polymer that is incorporated into the setting solution. The powder is mixed with the setting solution to form a bone cement paste that either (a) sets into a hardened mass, or (b) is irradiated with electromagnetic radiation to form dry powders, the dry powders then being mixed with a second setting solution to form a radiation-assisted bone cement paste that sets into a hardened mass.

7 Claims, 16 Drawing Sheets

(56) References Cited

FOREIGN PATENT DOCUMENTS

| WO | WO 2008117043 A2 * | 10/2008 | ......... A61L 24/0089 |
|---|---|---|---|
| WO | WO 2010055483 A2 * | 5/2010 | ............. A61L 27/12 |

OTHER PUBLICATIONS

Wang et al., "Bone repair in radii and tibias of rabbits with phosphorylated chitosan reinforced calcium phosphate cements", Biomaterials, 2002, vol. 23, pp. 4167-4176.

Wang et al., "Structural characterization of phosphorylated chitosan and their applications as effective additives of calcium phosphate cements", Biomaterials, 2011, vol. 22, pp. 2247-2255.

Australian Patent Examination Report No. 1, Application No. AU 2013215158 dated Nov. 25, 2015.

Chinese 1st Office Action, Application No. CN 201380013370.2 dated Feb. 26, 2016.

European Search Report, Application No. EP 13742896.7 dated Sep. 7, 2015.

European Search Report, Application No. EP 13742896.7 dated Jan. 21, 2016.

Australian Examination Report No. 1, Application No. AU 2016204525, dated Feb. 9, 2017.

Borhan et al. "Evaluation of collodial silica suspension as efficient additive for improving physiochemical and in vitro biological properties of calcium sulfate-based nanocomposite bone cement", Journal of Material Science: Material Medicine, 2010, vol. 21, pp. 3171-3181.

Jalota et al. "Using a synthetic body fluid (SBF) solution of 27 mM $HCO_3$— to make bone subsitutes more osteointegrative," Materials Science and Engineering C, 2008, pp. 129-140.

Japanese Notifications of Reasons for Rejections, Application No. JP 2014-555693, dated Oct. 26, 2016.

Boistelle et al., "Morphology, Habit and Growth of Newberyite Crystals ($MgHPO_4$ $3H_2O$)", Journal of Crystal Growth, 1981, vol. 54, pp. 275-295.

Tamimi et al., "Biocompatibility of magnesium phosphate minerals and their stability under physiological conditions", Acta Biomaterialia, 2011, vol. 7, pp. 2678-2685.

Australian Examination Report No. 1, Application No. AU 2017232233, dated Aug. 9, 2018.

Klammert et al., "Phase composition, mechanical performance and in vitro biocompatibility of hydraulic setting calcium magnesium phosphate cement", Acta Biomaterialia, 2010, vol. 6, pp. 1529-1535.

Klammert et al., "In vivo degradation of low temperature calcium and magnesium phosphate ceramics in a heterotopic model", Acta Biomaterialia, 2011, vol. 7, pp. 3469-3475.

Japanese Notification of Reasons for Rejection, Application No. JP2017-185831, dated Jul. 24, 2018.

* cited by examiner

INJECTABLE, BIODEGRADABLE BONE CEMENTS AND METHODS OF MAKING AND USING SAME

CROSS-REFERENCE TO RELATED APPLICATIONS

This is a national stage application filed under 35 U.S.C. § 371 of international application PCT/US13/24040, filed under the authority of the Patent Cooperation treaty on Jan. 31, 2013, published; which claims the benefit of U.S. Provisional patent application Ser. Nos. 61/593,094 and 61/697,059, filed under 35 U.S.C. § 111(b) on Jan. 31, 2012 and Sep. 5, 2012, respectively. The entire disclosures of all the aforementioned applications are incorporated herein by reference for all purposes.

STATEMENT REGARDING FEDERALLY SPONSORED RESEARCH

This invention was not made with any government support, and the government has no rights in this invention.

FIELD OF THE INVENTION

This invention generally relates to bone cement compositions and methods of making, strengthening, and using bone cement compositions.

BACKGROUND OF THE INVENTION

There is no admission that the background art disclosed in this section legally constitutes prior art.

Conditions related to back pain account for more hospitalizations than any other musculoskeletal condition. The back is the body part most often involved in work-related disabilities. Back pain is the most prevalent medical disorder in industrialized societies. It is estimated that more than 75% of the United States population will be affected by low back pain over the course of their lifetime. According to the statistics from the National Institutes of Health, back pain is the second most common medical condition for which people seek treatment, accounting for more than 50 million physician office visits annually. Low back pain is the leading cause of disability in people younger than age 50.

In order to alleviate back pain, many people undergo surgical intervention. Implanted instrumentation is used in many types of spinal surgeries to help join vertebrae together and restore stability. Additionally, implants such as plates, rods, and screws help correct deformities and bridge spaces created by the removal of damaged spinal elements. Bone cement is desired in clinical situations to enable proper fixation of the implants. Bone cement is also used in a wide variety of other medical and dental applications, such as in the repair of cranio-maxillofacial defects, tooth fillings, or spinal fusions.

The bone cements commonly used are poly methyl methacrylate (PMMA) cements. Bone cements made from PMMA have several disadvantages. Namely, methacrylates and methacrylic acid are known irritants to living tissue. PMMA-based cements can generate free radicals in vivo, which can damage surrounding tissue. PMMA-based cements are also not biodegradable, and the polymerization reaction involving PMMA is highly exothermic, possibly causing damage to surrounding tissue when cured.

Another problem with many conventional bone cement formulations is the necessity of mixing and storing two or more solid powder ingredients, which reduces their batch-to-batch reproducibility and shelf life. Homogeneous mixing of two solids is not an easy task. Optimal cements should be able to set in a liquid medium during the normal setting time without being washed away. This is important for injectability and cohesiveness. Both of these issues can be enhanced by incorporating a polymer in the setting solution. However, cement compositions containing polymers with two solid ingredients still have poor injectability because homogeneous mixing of two solid ingredients is not easy.

Some possible alternatives to PMMA-based cements are cements made from various alkaline earth phosphates. These include calcium phosphate cements, magnesium phosphate cements, and strontium phosphate cements. Of all alkaline earth phosphates, Ca—P cements, or CPCs, are the most common. CPCs are based on different compounds within the CaO—$P_2O_5$ (Ca—P) binary system. These compounds include Ca-hydroxyapatite, $Ca_{10}(PO_4)_6(OH)_2$ or simply hydroxyapatite, which is most well known due to its similarity to natural bone mineral. Other compounds in the Ca—P binary system include tetracalcium phosphate (TTCP, $Ca_4(PO_4)_2O$), tricalcium phosphate [α-TCP, α-$Ca_2(PO_4)_2$ and β-TCP, β-$Ca_3(PO_4)_2$], dicalcium phosphate anhydrous (DCPA, monetite, $CaHPO_4$), di-calcium phosphate dehydrate (DCPD, brushite, $CaHPO_4.2H_2O$), and octacalcium phosphate (OCP, $Ca_8H_2(PO_4)_6.5H_2O$). CPCs offer several advantages over PMMA-based cements, such as greater malleability, allowing the cement to better adapt to a defect's site and shape. CPCs also offer better biocompatibility, bioactivity, osteoconductivity, and bioresorbability.

Mg—P cements (MPCs) in the market are mainly based on the composition of $MgNH_4PO_4$, formed via reaction between acid part (ammonia salts) and base part (MgO or $Mg(OH)_2$), resulting in exothermic phenomena. However, the release of ammonia during setting and degradation of MPCs compromises the biocompatibility of the cements. Sr—P cements (SPCs) are Ca—P or Mg—P cements doped with strontium. Strontium can promote cell growth and provides radio opacity.

It would be desirable to formulate bone cement compositions that are easily made and possess improved strength, mechanical properties, and bioactivity. It would be further desirable if the properties of such bone cements allow them to be readily used in the surgical theater.

SUMMARY OF THE INVENTION

In a first aspect of this invention, there is provided a bone cement composition made from mixing one powder component, a setting solution, and a biocompatible polymer. The powder component comprises a basic source of calcium, magnesium, or strontium. The setting solution comprises phosphoric acid. A biocompatible polymer is incorporated into the setting solution prior to mixing with the powder. In certain embodiments, the biocompatible polymer is chitosan and is surface-phosphorylated, then incorporated into the setting solution at a concentration ranging from about 0% to about 10% by weight of the setting solution. Upon mixing, a paste forms that either (a) hardens into a solid mass some period of time after mixing the powder with the setting solution, or (b) is irradiated with electromagnetic radiation to form dry powders that are then mixed with a second setting solution to form a bone cement paste that sets into a hardened mass. In certain embodiments, the cement has a setting time of from about 30 minutes to about 60 minutes.

In a second aspect of this invention, there is provided a method of reducing the exothermicity of bone cement compositions. The method involves irradiating a bone cement paste (made from acid-base reactions) with electromagnetic radiation to form dry powders, then mixing the dry powders with a setting solution comprising water, saline, or nanosilica sol to form a bone cement paste that sets into a hardened mass. The reaction does not change the pH and does not release any heat. The method described herein also produces strengthened bone cement compositions suitable for weight-bearing applications.

Further disclosed herein are methods of making bone cement. One method comprises mixing a single powder component with a setting solution and a biopolymer to form a paste, then allowing the paste to set into a hardened mass. Another method comprises forming a bone cement paste from an acid-base reaction, irradiating the bone cement paste with electromagnetic radiation to form dry powders, and mixing the dry powders with a setting solution comprising water, saline, or nanosilica sol to form a radiation-assisted bone cement paste that sets into a hardened mass after a period of time.

Further disclosed herein is a method of producing a settable CPC/MPC/SPC with minimum exothermic properties. Further disclosed are methods of using a bone cement to treat a subject, to deliver a drug, to increase the biocompatibility of titanium implants, to increase the strength of a calcium sulfate dehydrate cement, to fill a tooth defect, to fill a hole or cavity in a bone, and to replace or treat weakened or collapsed vertebrae.

Further disclosed are various kits for making a bone cement composition as described herein.

Various aspects of the invention will become apparent to those skilled in the art from the following detailed description of the preferred embodiments, when read in light of the accompanying drawings.

BRIEF DESCRIPTION OF THE DRAWINGS

The following drawings may contain hidden features or elements shown in dotted lines and may include phantom views of various components or elements shown in dashed-dotted lines.

DETAILED DESCRIPTION

Figure 1:
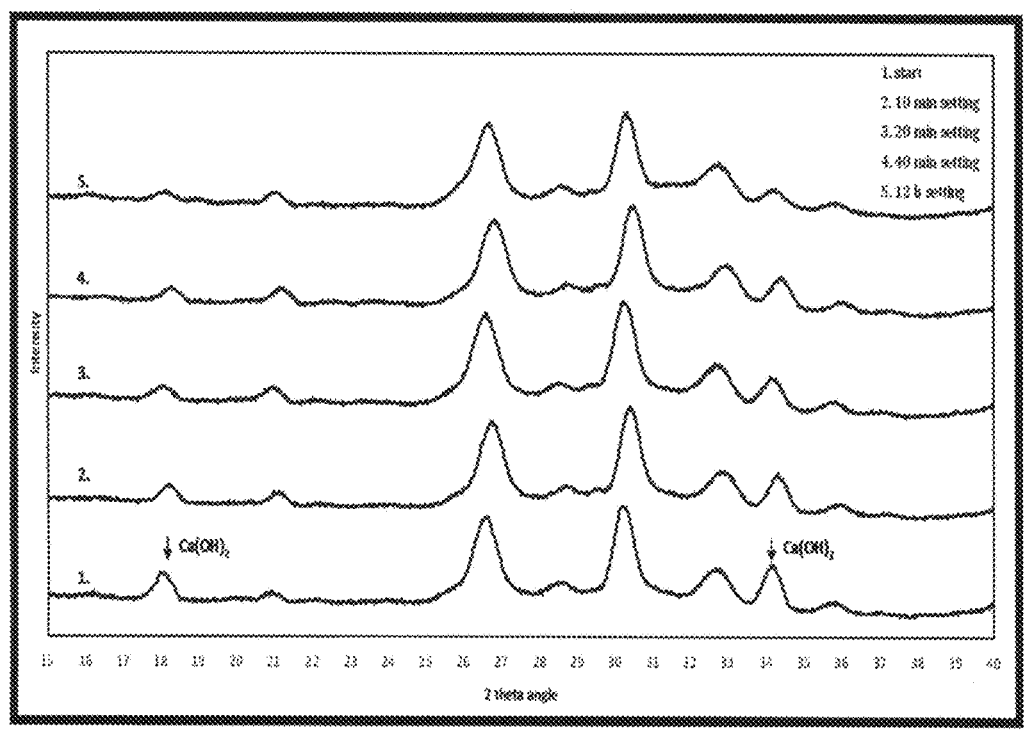
FIG. 1 is a comparison of XRD patterns for monetite cement pastes formed between ten minutes and twelve hours of setting.

Throughout the entire specification, including the claims, the word "comprise" and various of the word, such as "comprising" and "comprises" as well as "have," "having," "includes," and "including," and variations thereof, means that the named steps, elements, or materials to which it refers are essential, but other steps, elements, or materials may be added and still form a construct within the scope of the claim or disclosure. When recited in describing the invention and in a claim, it means that the invention and what is claimed is considered to be what follows and potentially more. These terms, particularly when applied to claims, are inclusive or open-ended and do not exclude additional, unrecited elements or method steps.

Various embodiments are described herein in the context of composition, and method, formula, system, and/or process for preparing, bone cements having improved mechanical properties. Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" herein indicate that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

In the interest of clarity, not all of the routine features of the implementations or processes described herein are shown and described. It will, of course, be appreciated that in the development of any such actual implementation, numerous implementation-specific decisions will be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking for those of ordinary skill in the art having the benefit of this disclosure.

A state-of-the-art bone cement composition should meet the following criteria: (1) the composition should use one solid component, thus enabling easy mixing; (2) the composition should use solids that do not need high-temperature processing; (3) the composition should use a setting solution of an aqueous nature; (4) the hardening (setting) process should not be exothermic so that no tissue necrosis takes place; (5) the final phosphate phase should be biodegradable, for example MgP, SrP, TCP, DCPA, or DCPD, thus enabling regeneration of bone tissues; (6) the composition should be injectable (i.e., of the correct rheological property) to fill a bone defect; (7) the composition should harden in a suitable timeframe to give a surgeon an optimum window of opportunity to inject the cement before hardening takes place; (8) the cement should develop strength of the trabecular bone within a window of ten minutes to two hours for the weight bearing of the patient and ultimately developing even higher strength within 24 hours after the operation; (9) the cement should be radio-opaque for quick identification by X-rays; (10) the cement should be biocompatible and biodegradable, as determined by in vitro testing; and (11) the cement should maintain the above characteristics in vivo as well.

In accordance with the above, provided herein is a bone cement composition made from a single powder component comprising a basic source of calcium, magnesium, or strontium, and a setting solution comprising $H_3PO_4$. In certain embodiments, the powder comprises $Ca(OH)_2$ or $Mg(OH)_2$, and the setting solution further comprises a biocompatible polymer, deionized water, a buffer such as $NaHCO_3$, and citric acid monohydrate. In particular embodiments wherein the powder is $Ca(OH)_2$, the resulting bone cement is a dicalcium phosphate anhydrous ($CaHPO_4$, also known as monetite or DCPA) cement that dispenses with several problems in conventional bone cement formulations. The CPCs currently available commercially are either apatite CPCs (such as α-BSM®, BoneSource®, Calcibon®, and Biopex®) or brushite CPCs (such as ChronOS Inject®, Eurobone®, and VitalOS®). However, monetite is a good alternative to apatite and DCPD cements because it has similar chemical composition and solubility to DCPD, it exhibits desirable properties that support bone regeneration, and it does not reprecipitate into apatite in vivo.

The monetite bone cement disclosed herein is based on an acid-base reaction between $H_3PO_4$ and $Ca(OH)_2$, with $NaHCO_3$ as a pH buffer. The monetite cement is made from a single powder component and a setting solution. The powder comprises $Ca(OH)_2$, which is readily available commercially and relatively inexpensive. The $Ca(OH)_2$ powder can be used without any further treatments or additives, and is not subjected to high temperatures during synthesis. The setting solution comprises phosphoric acid ($H_3PO_4$). In certain embodiments, a biocompatible polymer is incorporated into the setting solution to provide cohesiveness to the composition. The biopolymer further enhances the mechanical properties of the cement by providing a toughening mechanism against the propagation of a crack.

In certain embodiments, the biocompatible polymer comprises chitosan [(1-4)-2-amino-2-deoxy-β-D-glucan] and is present from about 0% to about 20% by weight of the total composition. More particularly, the chitosan is present from about 1% to about 5% by weight of the total composition. Chitosan is a compound found primarily in the exoskeletons of arthropods and has several desirable attributes for incorporation into cement compositions. It has a polycationic carbohydrate structure similar to that of hyaluronic acid, an extracellular matrix molecule. Chitosan has a cationic nature that provides a suitable substrate for cell adhesion and prevention of washout in a cavity. Chitosan is both biocompatible and bioactive (e.g., osteoinductive), as well as haemostatic. While liquid at room temperature, chitosan tends to gel at higher temperature such as the physiological temperature of 37° C. These properties contribute to the cement composition's injectability, bioactivity, cohesiveness, and improved mechanical properties.

In certain embodiments, the chitosan is surface-phosphorylated prior to being incorporated into the setting solution. One method of achieving this surface modification is by dissolving chitosan in orthophosphoric acid, urea, and N,N-dimethyl formamide, heating and stirring the mixture, then pouring the mixture into water and filtering it to collect surface-phosphorylated chitosan particles. Phosphorylation improves the adhesion of the chitosan to the cement.

The setting solution comprises $H_3PO_4$ but may further comprise deionized water and a suitable buffer, such as sodium bicarbonate ($NaHCO_3$) dissolved in water, to increase the pH of the setting solution, as well as citric acid monohydrate (CAM) to improve the handling of the final paste. In some embodiments, the powder component is mixed with deionized water to form a basic solution which is then mixed with the setting solution, while in other embodiments the powder component is mixed directly with the setting solution. In one embodiment, the powder and setting solution are mixed in a powder-to-liquid ratio of about 1 g per 0.4 mL. In another embodiment, the powder-to-liquid ratio is about 1 g per 0.6 mL. Many other ratios are possible. The powder-to-liquid ratio is easily changed by using different amounts of deionized water in the setting solution.

Upon mixing with the setting solution, a paste is formed by redox reactions between the $H_3PO_4$ and the $Ca(OH)_2$. The paste is a monetite (DCPA) cement that sets into a hardened mass between 30 and 60 minutes after mixing. The hardened monetite cement is stable in deionized water at 37° C. due to a thin apatitic film on its surface, but converts to apatite readily in carbonated solutions at a slightly elevated temperature of 95-100° C. The monetite cement has a higher solubility at neutral pH in physiological solutions than other CPCs and stimulates apatite formation in simulated body fluids after a relatively short time. Increased pH values also lead to hydrolysis of monetite to form apatite.

Currently available CPCs are based on a powder component comprising at least two or more CaP or Ca- or P-containing phases. The components of these powder mixtures may undergo solid state reactions that limit their shelf life and storage conditions. The requirement of only one powder component for the monetite cement disclosed herein is thus advantageous. The monetite cement also exhibits a higher in vivo resorbability in comparison to apatitic cements. Furthermore, unlike α-TCP and TTCP powders, the monetite cement powders can be synthesized at room temperature, alleviating the need to quench the cement phases to ambient temperatures which may require delicate grinding and cause contamination or undesired hydrolysis during grinding.

In addition to a variety of surgical applications discussed below, the monetite bone cement disclosed herein can be used as a coating on titanium implants that converts to apatite, making this a useful technique for increasing the biocompatibility of titanium implants. Also, the monetite bone cement can be added to calcium sulfate dehydrate (CSD) cements to significantly increase the mechanical properties of the CSD cements.

Further disclosed herein is a method of reducing the exothermicity of alkaline earth phosphate bone cements such as the monetite cement described above, and a series of alkaline earth phosphate bone cements with significantly reduced exothermicity. The method can be utilized with any cement paste formed from an acid-base reaction and produces alkaline earth cements with minimum exothermicity capable of use in weight-bearing applications. The process involves subjecting a cement paste comprising reactants of powder and liquid in an optimal ratio (before the paste sets) to electromagnetic radiation with frequencies between about $10^6$ Hz to about $10^{22}$ Hz, such as microwaves, to produce dried CPC/MPC/SPC powders. The irradiation preserves the cement in its initial reaction stage and causes the paste to form a brittle mass. The irradiation also removes water to stop the hydrolysis and crystallization of CPC/MPC/SPC precursors, and renders all CPC/MPC/SPC precursors inactive. The brittle mass is crushed into fine powders. The fine powders are then mixed with a setting solution comprising water, saline, or nanosilica sol. Upon contact with the setting solution, hardening of the paste continues and the cement strength increases. From this process, a viscous and moldable paste is obtained with minimum exothermicity. The paste sets to a firm mass after a period of time.

The cements produced using this electromagnetic radiation-assisted technique have improved hardening and mechanical properties with significantly minimized exothermicity and no change in pH. When nanosilica sol is used as the setting solution, further improvement to the mechanical properties of the cements compared to water or other aqueous solution is achieved. This is due to the nanosilica sol providing amorphous calcium silicate hydrate (CSH) gel for initial strength reinforcement and increased bioactivity. As time proceeds, the CSH gel polymerizes and hardens to provide a solid network to support the cement, thereby providing more strength and promoting bioactivity of the cement. It should be noted that the addition of nanosilica, or any other additive, can alter the desired powder-to-liquid ratio needed to produce the final cement.

Some Si-containing CPCs/MPCs/SPCs are already available commercially with adequate osteoconducitivty. However, commercially available Si-containing cements are referred to as silicon or silicate "substituted" cements. "Substitution" in this context means Si enters into the relevant CPC/MPC/SPC lattice (crystal structure), thus modifying osteoconductivity and osteoinduction. Such cements are typically not suitable for orthopedic applications because they are difficult to synthesize, have a long setting time, show poor mechanical strength for load-bearing applications, and may require high-temperature melting. (See Gibson, I. R., Best, S. M., Bonfield, W., Chemical Characterization of Silicon-Substituted Hydroxyapatite, J Biomed Mater Res 1999; 44:422-428.) In the CPC—$SiO_2$, MPC-$SiO_2$, and SPC—$SiO_2$ compositions presently disclosed, Si does not modify the lattice in any way. Rather, as disclosed herein, Si provides a strong bond between the cement particulates without deteriorating the osteoinduction or osteoconductivity. The resulting composition shows enhanced biocompatibility, bioactivity, and mechanical performance compared to conventional CPCs/MPCs/SPCs. The osteoinduction and osteoconductivity are mainly provided by the specific phosphate phase formed. In certain embodiments, the cement is monetite (DCPA), but the same mechanism applies to MPCs or SPCs.

The cements disclosed herein are useful for repairing a wide variety of orthopedic conditions. By way of non-limiting example, the cements may be injected into the vertebral body for treatment of spinal fractures, injected into long bone or flat bone fractures to augment the fracture repair or to stabilize the fractured fragments, or injected into intact osteoporotic bones to improve strength. The cements are useful in the augmentation of a bone-screw or bone-implant interface. The cements may also be formed into bone-filling granules to replace demineralized bone matrix materials. The cements disclosed herein provide an elastic modulus nearer to that of bone than conventional bone cements while being biodegradable, allowing the cement to be replaced by natural bone but at the same time mimicking the properties of normal bone and being able to sustain weight-bearing. Because of their enhanced weight-bearing capacity, the cements disclosed herein can provide scaffold support for various types of vertebral fracture and could be used in tibia plateau reconstruction, wrist fracture reconstruction, calcaneal reconstruction, and prophylaxis strengthening of the hip bone. Further, because of their enhanced biocompatibility and bioactivity, the cements disclosed herein may be used as delivery vehicles for drugs, genes, proteins, cells, DNAs, or other molecules.

Additionally, the cements are useful as bone filler in areas of the skeleton where bone may be deficient. In this context, the cements are intended to fill, augment, and/or reconstruct maxillofacial osseous bone defects, including periodontal, oral, and cranio-maxillofacial applications. The cements are packed gently into bony voids or gaps of the skeletal system (i.e., extremities, pelvis, and spine), including use in postero-lateral spinal fusion or vertebral augmentation procedures with appropriate stabilizing hardware. The cements may be used to fill defects which may be surgically created osseous defects or osseous defects created from traumatic injury to the bone. In certain embodiments, the cements provide a bone void filler that resorbs and is replaced by bone during the healing process.

Injectability and cohesiveness are clinically important issues related to the use of any bone cement. When the repair of a large defect is underway, a successful bone cement composition should flow smoothly and homogeneously, resulting in eventual uniform resorption. Embodiments of the bone cement formed from the radiation-assisted technique wherein the setting solution comprises nanosilica gel have improved injectability and cohesiveness. The exothermic properties of a bone cement are also clinically important. Because the silica-monetite cement disclosed herein gives off little heat, the silica-monetite cement does not cause necrosis of surrounding tissue and could be used as a drug delivery device. Due to the cement's increase in strength from the nanosilica bonding, the silica-containing cements described herein can be used for weight-bearing applications. Examples of weight-bearing applications include use in osteoporotic vertebral compression fractures in the spine and other traumatic fractures like tibia plateau fractures.

Various additives may be included in any of the compositions described herein to adjust their properties and the properties of the hardened cements produced. Examples of suitable additives include proteins, osteoinductive and/or osteoconductive materials, X-ray opacifying agents such as strontium phosphate or strontium oxide, medicaments, supporting or strengthening filler materials, crystal growth adjusters, viscosity modifiers, pore-forming agents, antibiotics, antiseptics, growth factors, chemotherapeutic agents, bone resorption inhibitors, color change agents, immersing liquids, carboxylates, carboxylic acids, α-hydroxyl acids, metallic ions, or mixtures thereof. Other suitable additives include substances that adjust setting times (such as pyrophosphates or sulfates), increase injectability or cohesion (such as hydrophobic polymers like collagen), alter swelling time, or introduce macroporosity (such as porogens).

If a reduced particle size of a particular cement composition disclosed herein is desired for a certain application, such particle reduction can be accomplished by using, for example, an agate pestle and mortar, a ball mill, a roller mill, a centrifugal-impact mill and sieve, a cutter mill, an attrition mill, a chaser mill, a fluid-energy mill, and/or a centrifugal-impact pulverizer. Particle size reduction may be desired for treating bone defects through a method that involves breaking up the hardened bone cement into pellets and filling a hole or cavity in the bone with the pellets.

The cements disclosed herein may be supplied to the user in a variety of forms, including as powders or as a powder mixture which is later mixed with a solvent to make slurry or putty, or as a pre-mixed putty which may a contain nonaqueous extender, e.g., glycerine and/or propylene glycol. The pre-mixed putty would allow the cement to set upon contact with water. Also, any of the cements disclosed herein can be delivered via injections. That is, a cement paste can be transferred to a syringe for injection into a mammalian body. Furthermore, the cements may be supplied with or in the instrumentation which is used to introduce the cement into the body. Examples of such instrumentation include, for example, a syringe, percutaneous device, cannula, biocompatible packet, dentula, reamer, file, or other forms which will be apparent to those of ordinary skill in the art. It is further envisioned that the bone cements disclosed herein could be delivered into the body in such a form as to be converted by bodily processes into the bone cement compositions disclosed herein.

It is contemplated that any of the cements disclosed herein may be made available to practitioners such as surgeons, veterinarians, or dentists via a kit containing one or more key components. A non-limiting example of such a kit comprises the dry and liquid components in separate containers, where the containers may or may not be present in a combined configuration. Many other kits are possible, such as kits comprising a source of electromagnetic radiation in order to prepare a radiation-assisted bone cement as described herein, kits comprising a pre-mixed putty instead of the powder and setting solution, and kits including a syringe or multiple syringes for injecting a bone cement composition formed from the components of such kit. The kits typically further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a CD-ROM or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Alternatively, the components to form a bone cement composition as described herein may be present as a packaged element. The cements are generally provided or employed in a sterilized condition. Sterilization may be accomplished by several methods such as radiation sterilization (e.g., gamma-ray radiation), dry heat sterilization, or chemical cold sterilization.

The bone cements disclosed herein may be further used for drug delivery. A drug can be dissolved in a bone cement paste, or a bone cement composition (before or after it sets) can be soaked in a solution comprising a drug, before the composition is injected or placed into or onto an anatomical location. The drug can then be released into the subject from the cement matrix. Embodiments resulting in sustained release of drugs are also envisioned, for instance by coating the cement matrix with polymers including PLA/PGA, polyacrylic acid, hydroxyl methylcellulose, and/or chitosan.

Example 1

A 15 mL setting solution was prepared by mixing 0.0032 g citric acid monohydrate, 6.0 g $NaHCO_3$, 3.0 mL $H_2O$, and 12 mL $H_3PO_4$ (86.2%). The pH of the setting solution was 0.25±0.01, and was stable over a shelf life of 6 months. The setting solution was stored in a tightly-capped glass bottle.

The powder component of the cement comprised only $Ca(OH)_2$ (>95%, Fisher Scientific). 1.235 g $Ca(OH)_2$ was mixed with 0.8 mL $H_2O$ in an agate mortar using an agate pestle. 1.5 mL of the setting solution was then added to the mixture, and an agate pestle was used to manually mix the powder and liquid, giving a paste-like substance at the end of 2.5 to 3 minutes. In a 37° C. environment, the paste hardened after 33 minutes, showing a strength of about 10 MPa.

Surface modification of chitosan for better bonding to monetite cement was achieved by mixing 3 g of 98% orthophosphoric acid, 15 g urea, 15 mL N,N-dimethyl formamide, and 1 g of chitosan microparticles or nanoparticles in a flask. The mixture was heated to 120° C. with magnetic stirring at 300 rpm for 1 hour. The mixture was poured into water and filtered to collect surface-phosphorylated chitosan particles.

Chitosan-incorporated monetite cement was prepared by adding the surface-phosphorylated chitosan particles to the setting solution with magnetic stirring at 300 rpm for 4 hours. When the chitosan particles were uniformly dispersed in the setting solution, the new setting solution was ready for further reaction. 1.235 g $Ca(OH)_2$ was mixed with 0.8 mL $H_2O$ in an agate mortar using an agate pestle. 1.5 mL of the new setting solution was then added to the mixture and the agate pestle was used to manually mix the powder and liquid to form a paste. After hardening, the monetite cement showed strength above 20 MPa.

Figure 2:
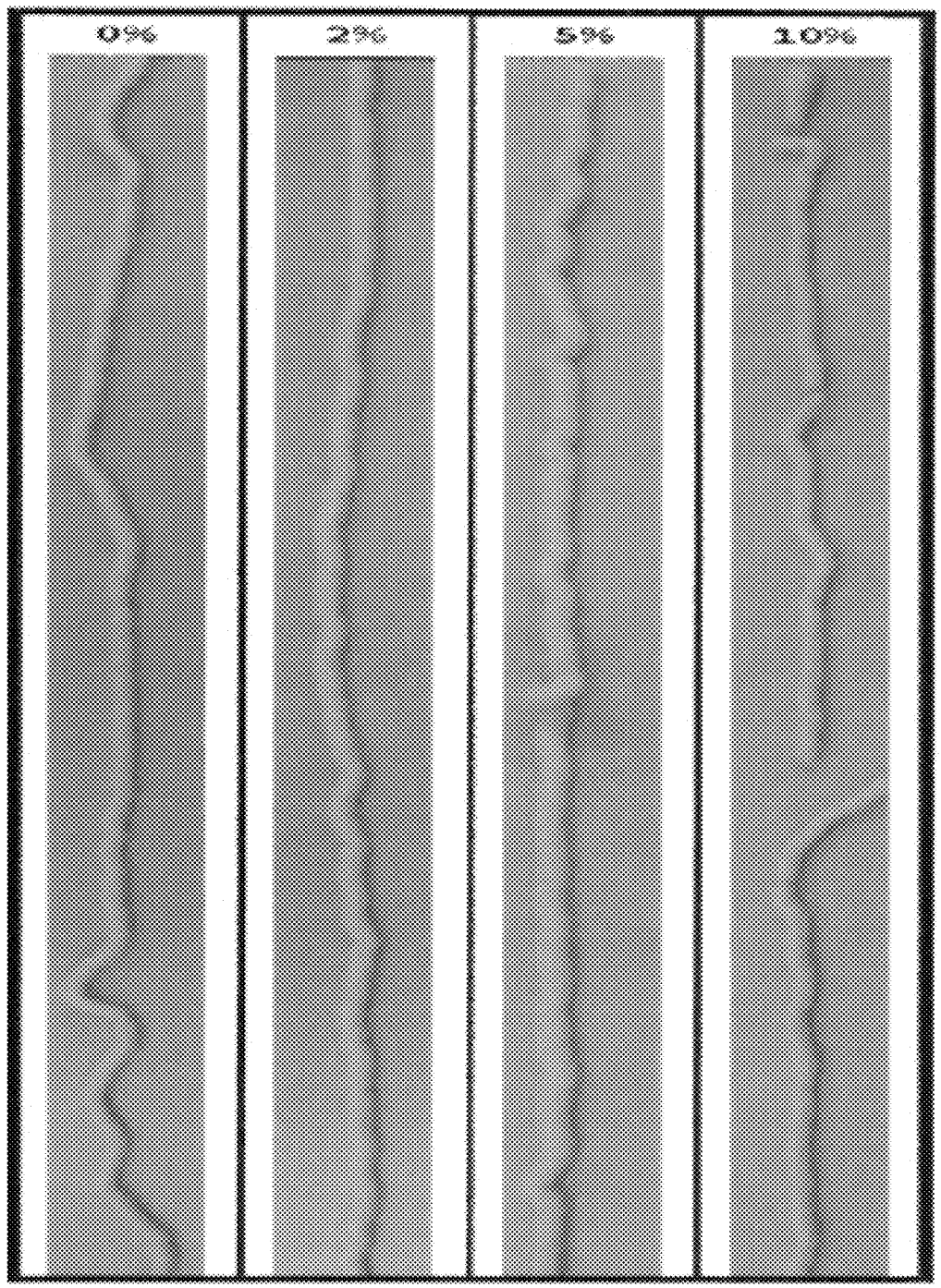
FIG. 2 illustrates the rheological properties of cements with varying amounts of chitosan.
Figure 3:
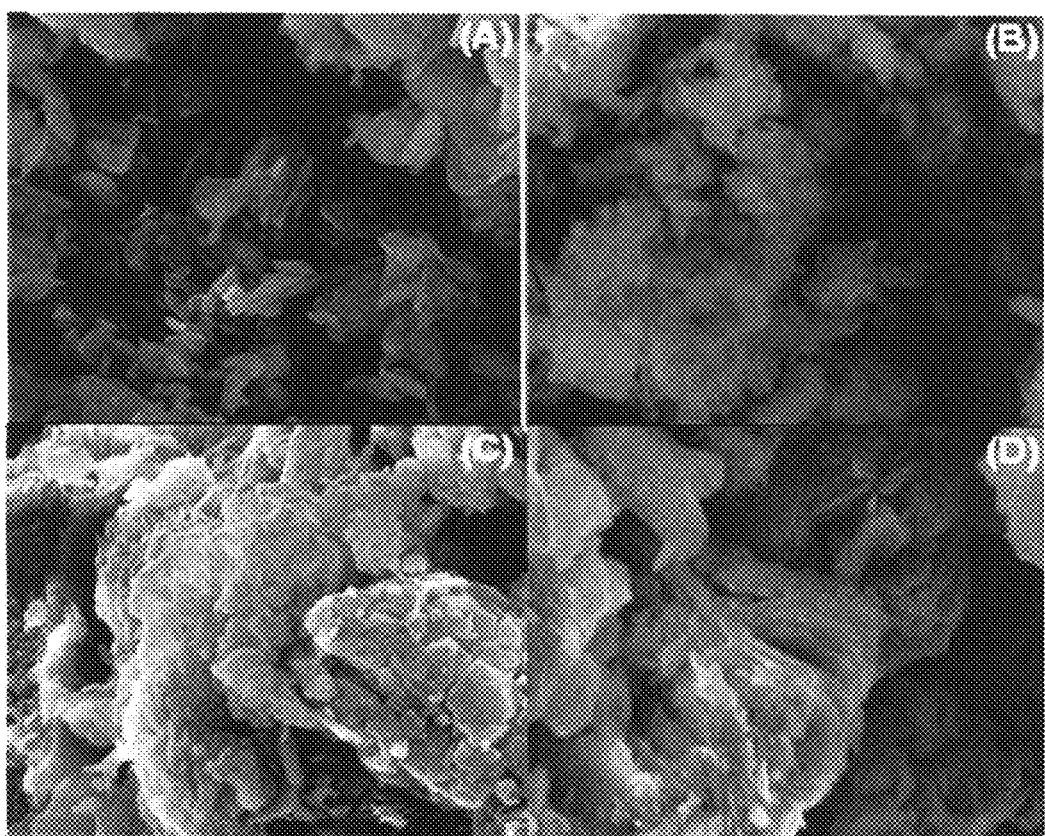
FIG. 3 is a series of SEM images of morphological structures for chitosan monetite composites with various content of chitosan by weight: 0% (A), 5% (B), 10% (C), and 20% (D).
Figure 4:
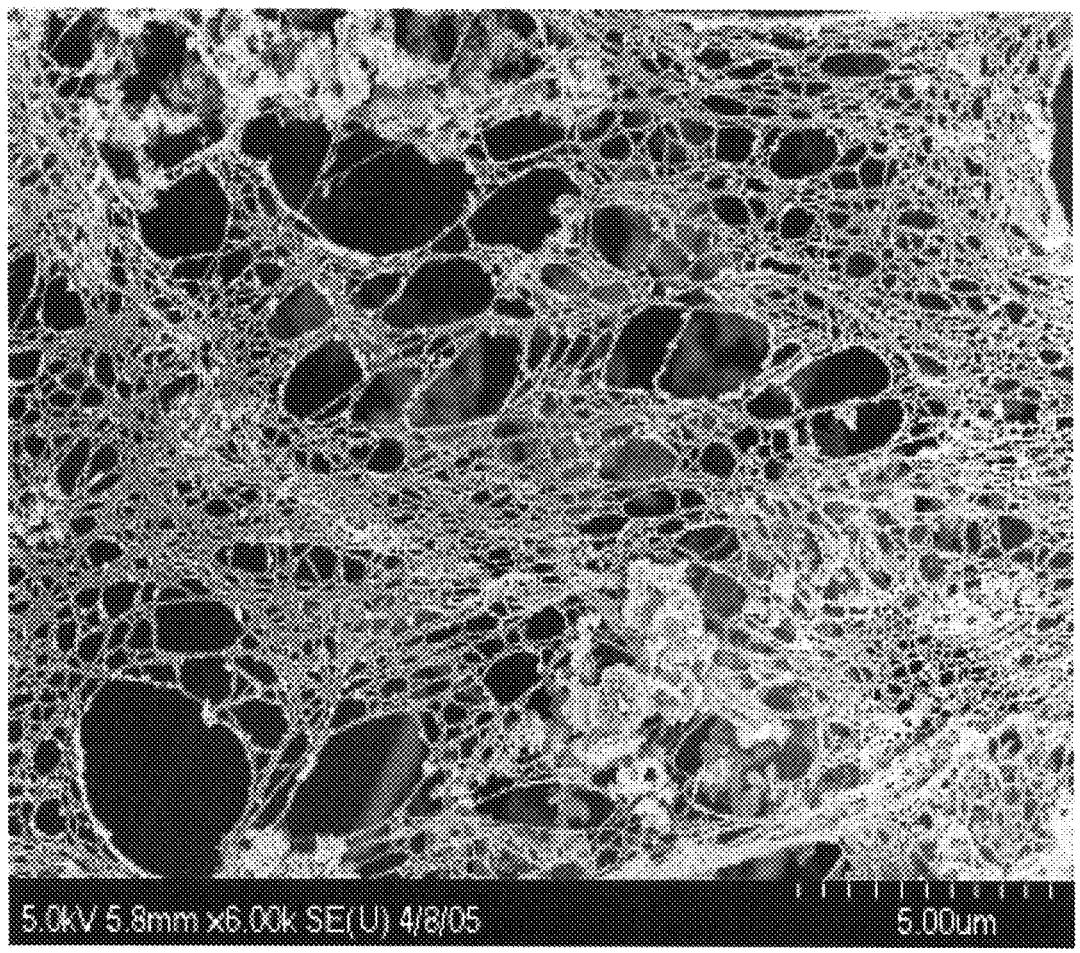
FIG. 4 is an SEM image illustrating the in vitro response of chitosan-containing cements.
Figure 5:
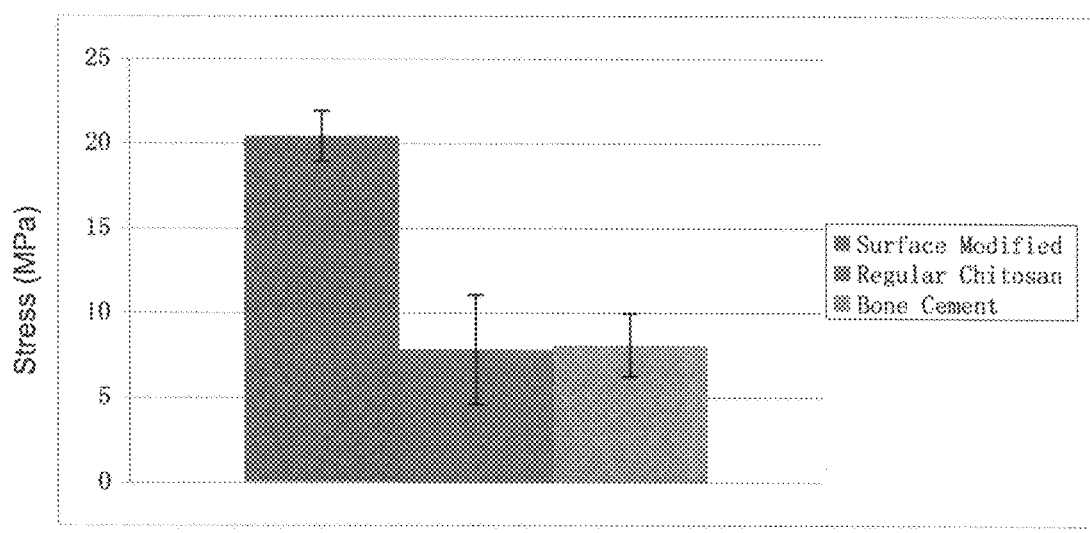
FIG. 5 is a graph showing a comparison of the compressive strength of monetite cement, monetite cement with commercially available chitosan, and monetite cement with surface-phosphorylated chitosan.
Figure 6:
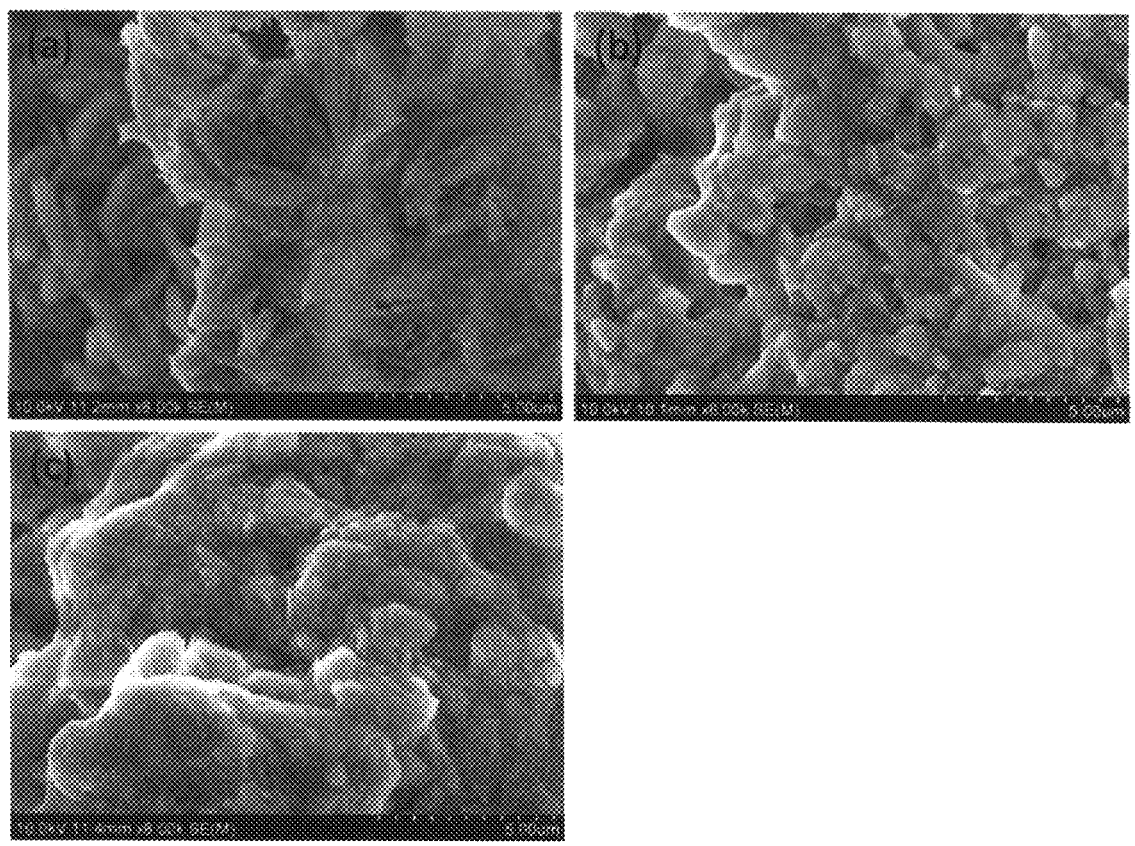
FIG. 6 shows SEM images of (a) monetite precursors formed after microwave treatment; (b) monetite cement formed by direct mixing with $Ca(OH)_2$ and $H_3PO_4$; and (c) hardened monetite cement after microwave treatment.
Figure 7:
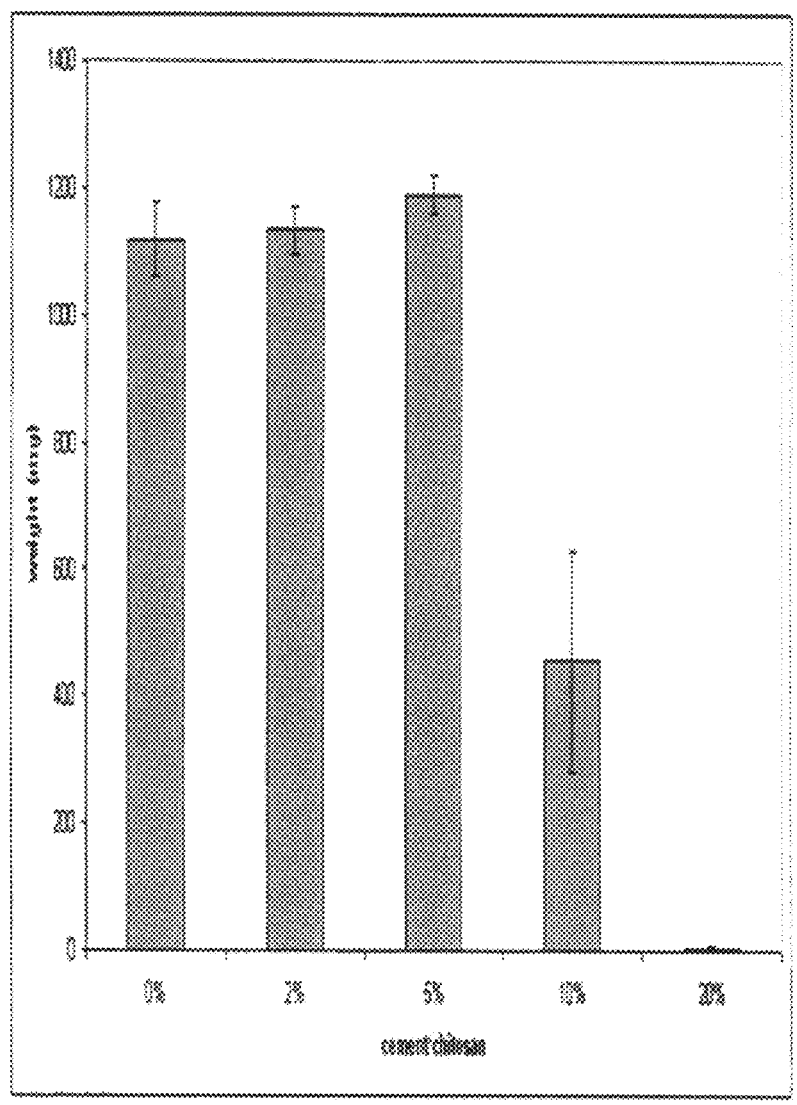
FIG. 7 is a graph showing the injectability properties of cements based on the percent of chitosan present in the cement.

FIG. 1 shows the formation of phases from the setting solution (with 5% added chitosan as a representative composition) at the intermediate time points 10 minutes, 20 minutes, 40 minutes, and 12 hours, by stopping the reactions in ethanol. All the peaks (other than $Ca(OH)_2$) are assigned to monetite (DCPA). FIG. 2 shows flow patterns of the injected cement paste with 0, 3, 5, and 10% by weight chitosan. The results show that with the addition of 10% chitosan, the cement paste does not flow continuously in spite of using just one solid ingredient. A 10% composition will not fill a bone defect cavity uniformly, resulting in non-uniform bone growth. FIG. 3 is an SEM micrograph of the cement with different chitosan content. FIG. 4 is an SEM micrograph of osteoblast cells on cement samples after 72 hours of seeding. The biocompatibility of the surface is shown by cell spreading, with cement particles visible underneath the osteoblasts. This proves the biocompatibility of the cement. FIG. 5 displays the compressive strength improvement of the cement after the addition of surface phosphorylated chitosan.

Example 2

Cement pastes were prepared by manually mixing $Ca(OH)_2$ with setting solution and DI water in an agate mortar by using an agate pestle. For preparing 15 mL of the setting solution, 0.0032 g of citric acid monohydrate (CAM, $C_6H_8O_7.H2O$, 100%), 6 g of sodium bicarbonate ($NaHCO_3$, >99.7%), 1.95 mL of DI water for diluting the setting solution, and 13.05 mL of phosphoric acid ($H_3PO_4$, 85%) solution as a source of phosphate, were mixed respectively. Initially, 0.6175 g of $Ca(OH)_2$ was mixed at least two minutes with 0.8 mL of DI water to form a paste with $Ca(OH)_2$ uniformly dispersed in the water. Finally, 0.75 mL of setting solution was added to the materials.

Figure 8:
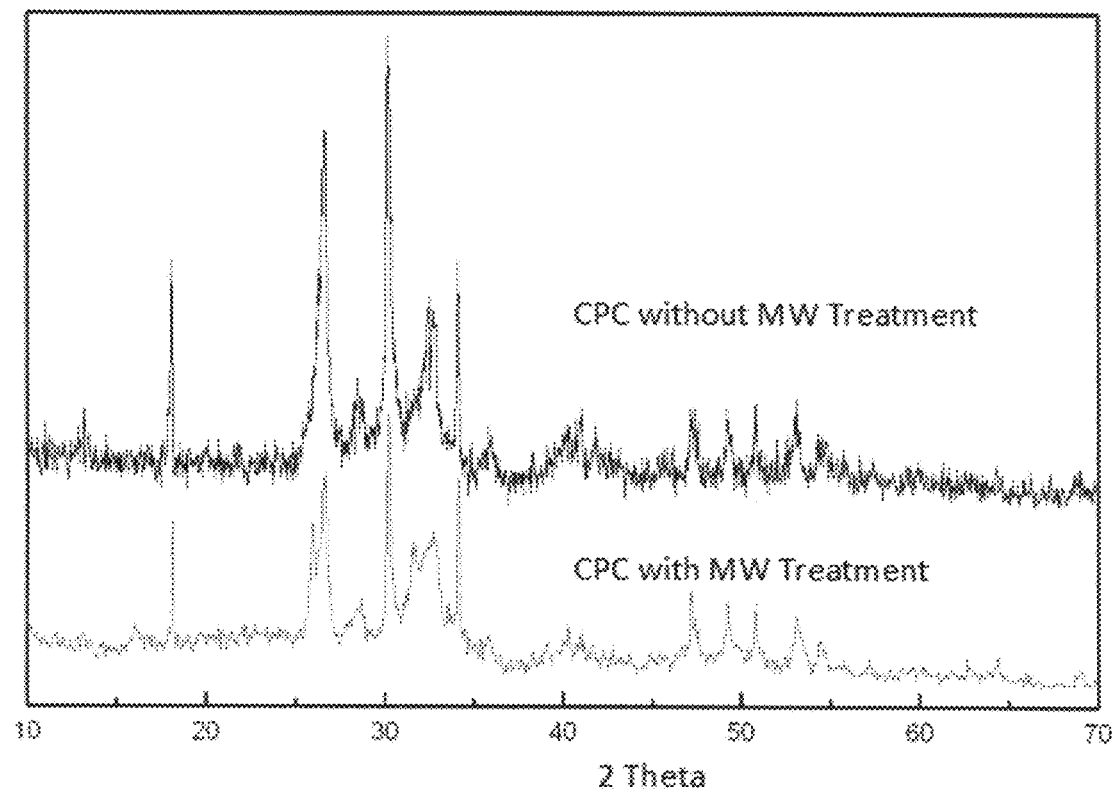
FIG. 8 is a comparison of XRD patterns of a monetite cement formed using a regular acid-base reaction, and a monetite cement formed using the microwave-assisted approach disclosed herein.
Figure 9:
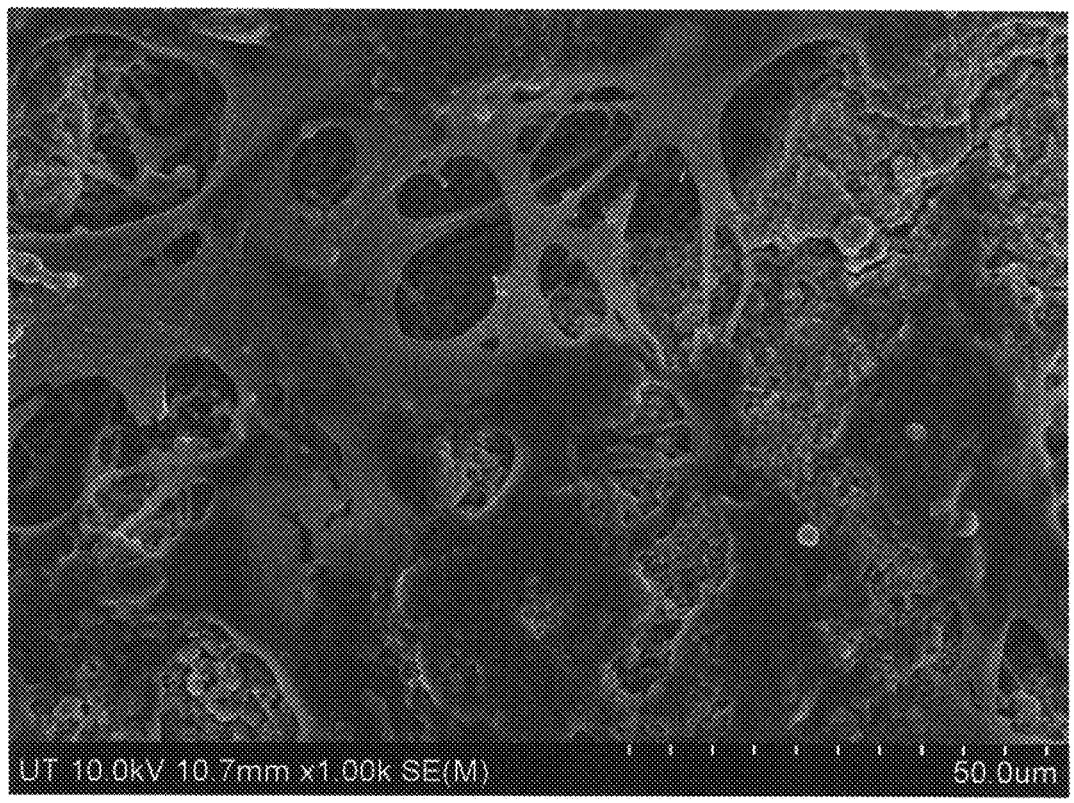
FIG. 9 is an SEM image of preosteoblast cells on monetite-silica cement samples 72 hours after seeding. The biocompatibility of the surface is shown by cell spreading. Cement particles are visible underneath the osteoblasts. This shows the biocompatibility of the cement.
Figure 10:
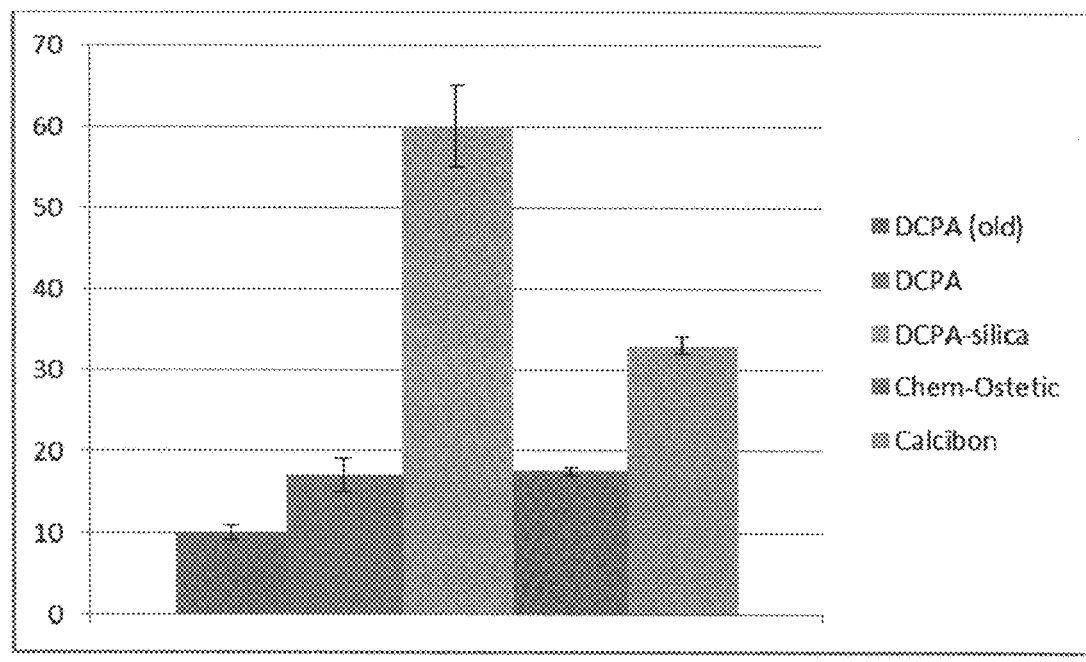
FIG. 10 shows compressive strength values of monetite-silica, monetite, monetite (old), Chem-ostetic, and calcibon cements. Microwave treatment can improve the compressive strength of monetite cement, comparable to non-load bearing cements on the market such as Chem-Ostetic. The addition of nanosilica sol to monetite significantly improves its strength, making the load-bearing of monetite-silica cement much higher than Calcibon, a commercial weight-bearing CPC on the market.
Figure 11:
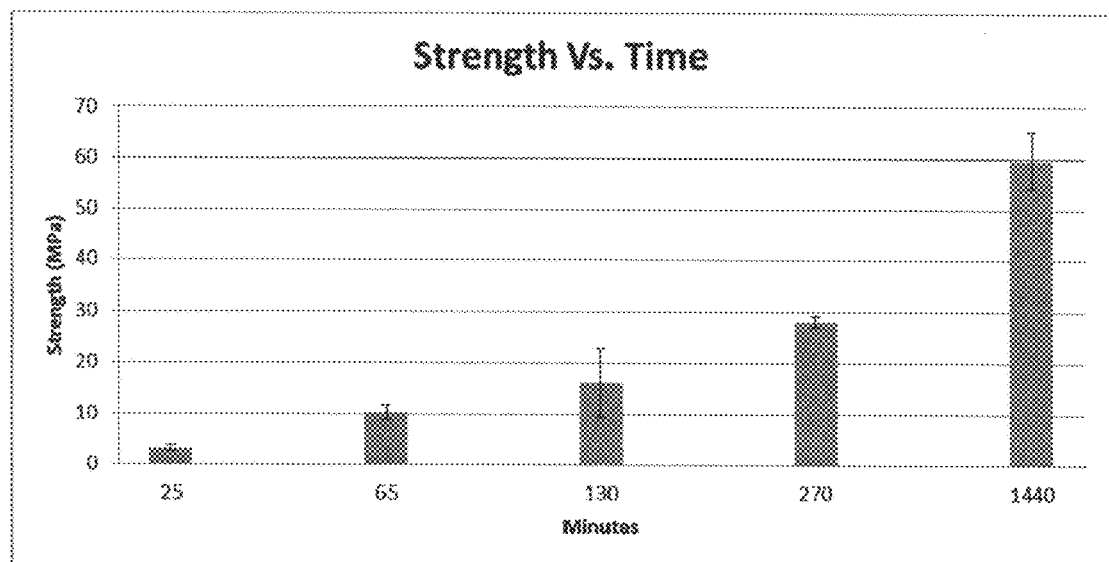
FIG. 11 is a graph showing compressive strength values of monetite-silica proceeding with time.
Figure 12:
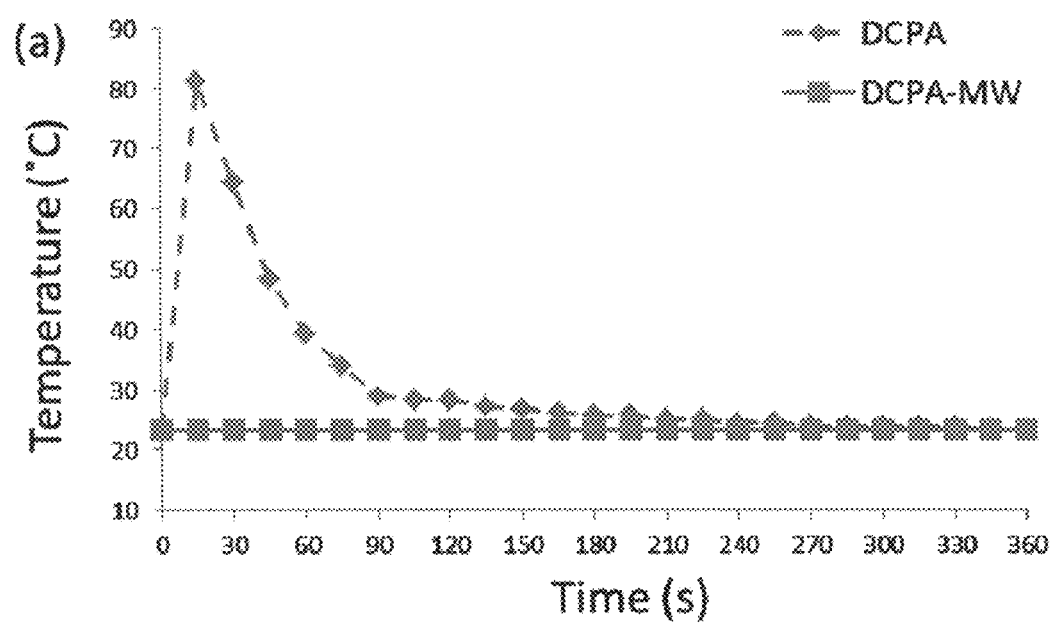
FIG. 12 is a graph of temperature over time, showing the difference in heat generated during mixing of monetite cement made with and without the microwave-assisted technique. As seen from this graph, the microwave-assisted technique generates significantly less heat.

The mixed paste was transferred to a household microwave with 1300 W energy input and baked for 5 minutes at maximum power. The resulted mass was crushed into fine powders using a pestle. 1 g of the monetite powders was then mixed with 0.5-0.8 mL water or nanosilica sol. In both cases, the formed paste could be shaped and injected, and was capable of self-setting at 45° F., 73° F., and 98.6° F. environments. The maximum compressive strength of the monetite-silicate cement reached 65 MPa, ideal for weight-bearing applications. FIG. 8 shows XRD patterns of monetite (DCPA) cements formed with and without using this radiation-assisted technique. FIG. 9 shows a scanning electron microscope (SEM) micrograph of preosteoblast cells on the monetite-silica cement samples after 72 hours of seeding. FIG. 12 shows the difference in heat generated during mixing reactants with water, with and without the microwave-assisted technique.

Example 3

Cement pastes were prepared by manually mixing $Mg(OH)_2$ with setting solution and DI water in an agate mortar by using an agate pestle. For preparing 15 mL of the setting solution, 0.0032 g of citric acid monohydrate (CAM, $C_6H_8O_7.H2O$, 100%), 6 g of sodium bicarbonate ($NaHCO_3$, >99.7%), 1.95 mL of DI water for diluting the setting solution, and 13.05 mL of phosphoric acid ($H_3PO_4$, 85%) solution as a source of phosphate, were mixed respectively. 2.47 g of $Mg(OH)_2$ was added to a mixture of 2 mL of DI water and 3 mL of setting solution to form a paste.

The mixed paste was transferred to a household microwave with 1300 W energy input and baked for 5 minutes at maximum power. The resulted mass was crushed into fine powders using a pestle. 2 g of the MPC powders were then mixed with 0.5-0.8 mL water or nanosilica sol. In both cases, the formed paste could be shaped and injected, and was capable of self-setting at 45° F., 73° F., and 98.6° F. environments.

Example 4

Figure 13:
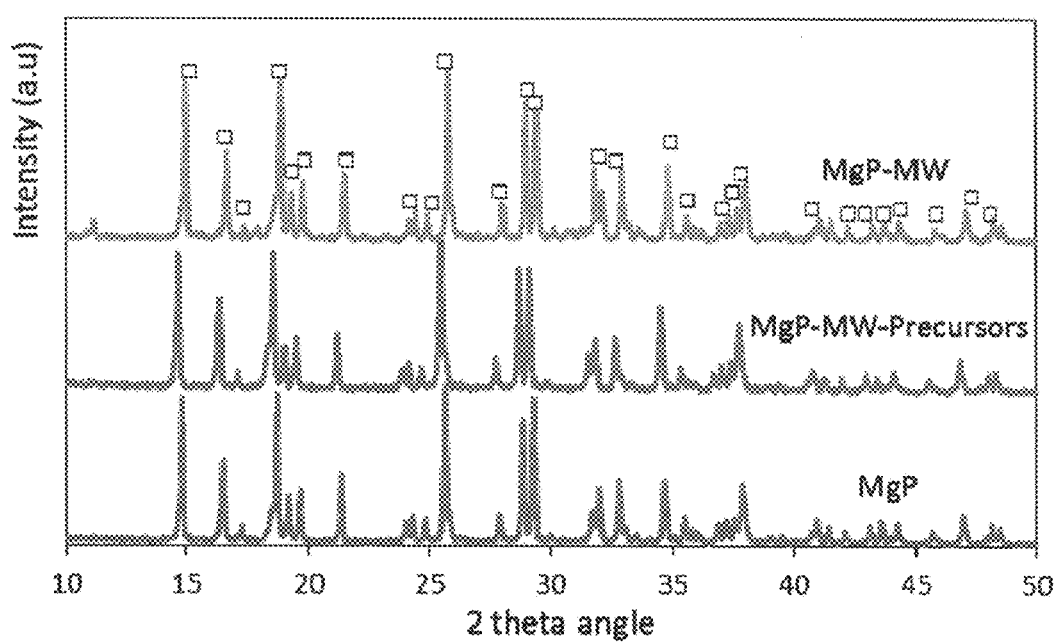
FIG. 13 displays XRD patterns of Mg—P precursors formed after microwave treatment, Mg—P cement formed by direct mixing with $Mg(OH)_2$ and $H_3PO_4$, and hardened Mg—P cement after microwave treatment.
Figure 14:
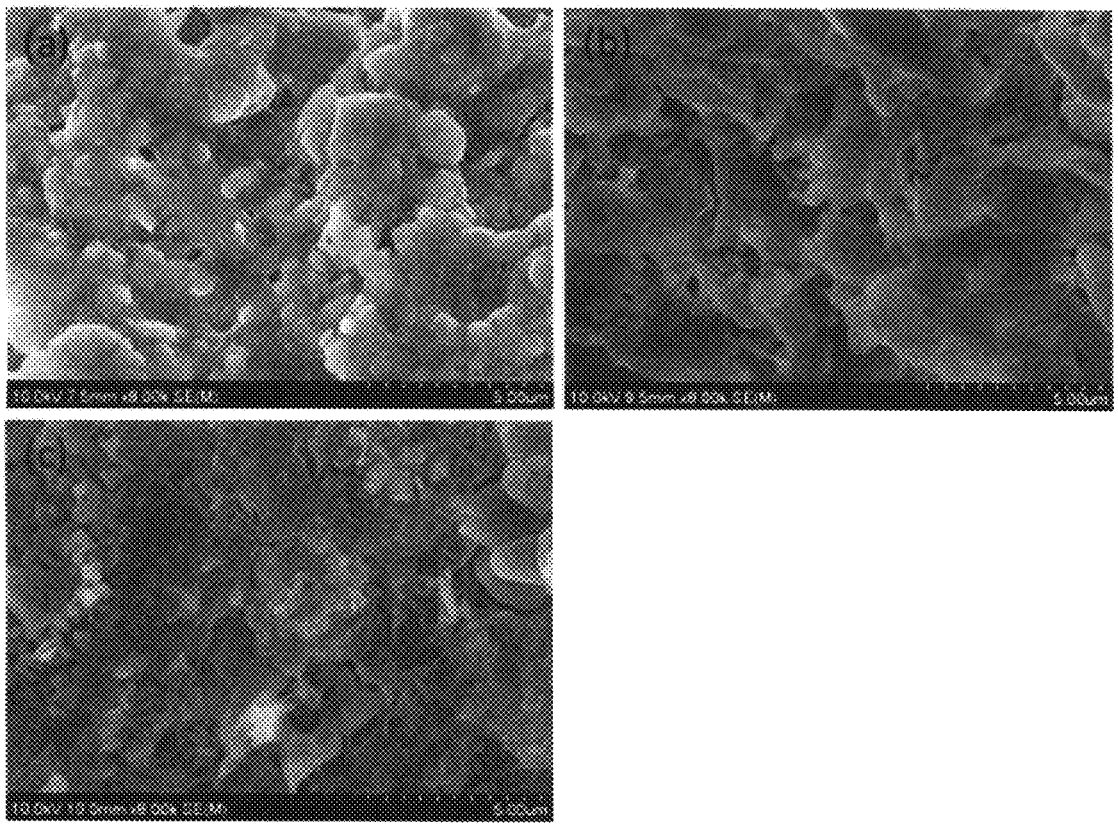
FIG. 14 shows SEM images of (a) Mg—P precursors formed after microwave treatment; (b) Mg—P cement formed by direct mixing with $Mg(OH)_2$ and $H_3PO_4$; and (c) hardened Mg—P cement after microwave treatment.

A cement paste was prepared by adding 1.235 g $Mg(OH)_2$ to a mixture of 0.5 mL DI water and 1.5 mL setting solution. The paste hardened into disk samples. The same paste, freshly prepared, was treated with microwaves for 10 minutes to prepare powders. The 1 g of synthesized powders was mixed with 0.4 mL DI water to form a paste that set into a hardened mass. FIG. 13 compares the XRD patterns of Mg—P precursors formed after microwave treatment, Mg—P cement formed by direct mixing with $Mg(OH)_2$ and $H_3PO_4$, and hardened Mg—P cement after microwave treatment. FIG. 14 shows SEM images of the precursors, cement formed from direct mixing, and cement formed after microwave treatment. The formed Mg—P is newberyite ($MgHPO_4.3H_2O$).

Figure 15:
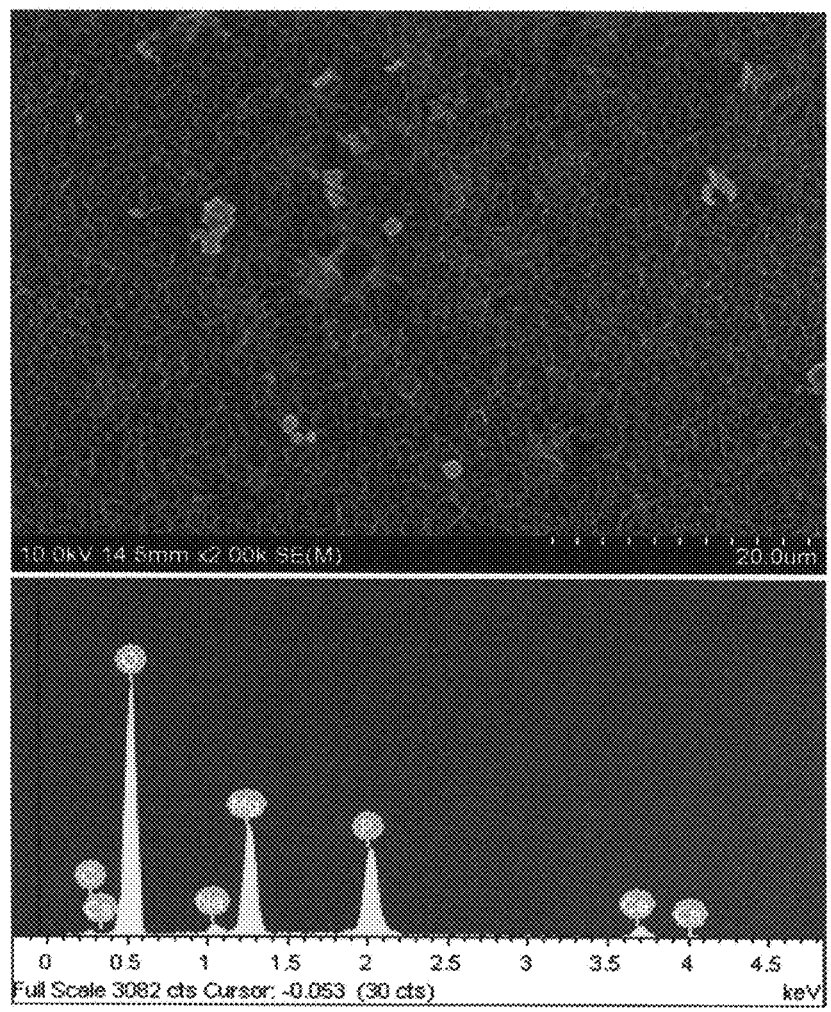
FIG. 15 is an SEM image of the Mg—P cement after 7 days incubation in simulated body fluid. The Mg—P cement converted into apatite with plate-like crystals and $Mg^{2+}$, $Ca^{2+}$, $Na^+$, and $PO_4^{3-}$ ions.
Figure 16:
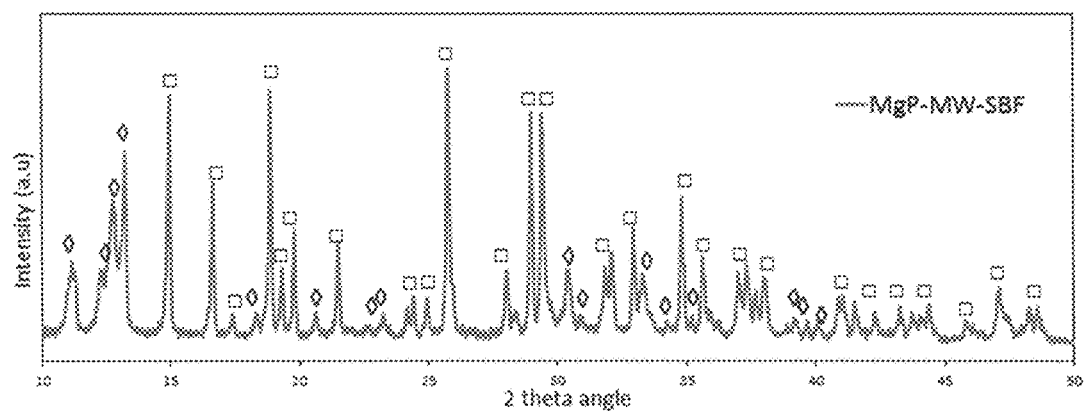
FIG. 16 is an XRD pattern of the Mg—P cement after 7 days incubation in simulated body fluid. The pattern indicates partial newberyite ($MgHPO_4.3H_2O$) was converted into bobierrite ($Mg_3(PO_4)_2.8H_2O$).

After 7 days incubation in simulated body fluid, the Mg—P cement was converted into apatite with plate-like crystals and $Mg^{2+}$, $Ca^{2+}$, $Na^+$, and $PO_4^{3-}$ ions. FIG. 15 shows an SEM image depicting this. FIG. 16 shows an XRD pattern of the Mg—P cement after 7 days SBF incubation, indicating partial newberyite ($MgHPO_4.3H_2O$) was converted into bobierrite ($Mg_3(PO_4)_2.8H_2O$).

Example 5

A strontium-containing cement was prepared using a setting solution of DI water. The reactants were $Mg(OH)_2$ and $H_3PO_4$ crystals. In the precursors' production, 3 g $Mg(OH)_2$ and 3.36 g $H_3PO_4$ were mixed with 3 mL water. After 1 minute of mixing, the formed paste was sent to a microwave oven for 5 minutes of maximum power heating treatment. The formed brittle material was crushed into fine powders. The powders were mixed with water containing $SrCl_2$ (0.01 g $SrCl_2$ to 1 mL water) at a weight/volume ratio of 3 g/mL to form a paste, which set after 5 minutes. Since such a small amount of $SrCl_2$ was added, no change to the XRD pattern of the resulting cement can be seen.

While various examples herein describe cements having Ca—P phases as the predominant component, other alkaline earths such as Sr can be added to synthesize doped Ca—P phases. In embodiments with Sr-doped Ca—P or Mg—P phases, the resulting cement has radio opacity and promotes cell growth. This will be readily apparent to practitioners skilled in the art.

The term "cement" herein is used interchangeably with paste, slurry, putty, cement formulation, and cement composition. The term "between" is used in connection with a range that includes the endpoints unless the context suggests otherwise. The term "shelf-life" herein means that the calcium phosphate mineral(s) will set when mixed with a solvent to form a cement after the powder has been stored in a sealed container for a predetermined period of time, most preferably for at least 6 months or more. The term "setting solution" herein means the solution leading to redox reactions. The term "injectable" as used in accordance with the present disclosure refers to when the calcium phosphate minerals are mixed with a solvent to form a cement paste and the paste is transferred to a syringe for injection into a mammalian body. The term "setting" means the hardening at room or body temperature of the paste formed by mixing a powder component and a setting solution as described herein.

Certain embodiments of the bone cement composition disclosed herein are defined in the examples herein. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A bone cement composition comprising:
   a magnesium phosphate comprising newberyite; a biocompatible polymer; and
   silica sol;
   wherein the bone cement composition is in the form of an injectable paste or a putty.

2. The bone cement of claim 1, wherein the biocompatible polymer comprises chitosan.

3. The bone cement of claim 1, wherein the biocompatible polymer is surface-phosphorylated.

4. A bone cement composition comprising:
   a magnesium phosphate comprising newberyite; and
   silica sol;
   wherein the bone cement composition is in the form of an injectable paste or a putty.

5. The bone cement composition of claim 4, further comprising an additive selected from the group consisting of: proteins, osteoinductive materials, osteoconductive materials, X-ray opacifying agents, medicaments, supporting or strengthening filler materials, crystal growth adjusters, viscosity modifiers, pore-forming agents, antibiotics, antiseptics, growth factors, chemotherapeutic agents, bone resorption inhibitors, color change agents, immersing liquids, carboxylates, carboxylic acids, α-hydroxyl acids, collagen, pyrophosphates, sulfates, and metallic ions.

6. The bone cement composition of claim 4, further comprising a nonaqueous extender comprising glycerine and/or propylene glycol, wherein the bone cement composition is in the form of a putty.

7. A bone cement composition comprising:
   a magnesium phosphate comprising newberyite; and
   silica;
   wherein the bone cement composition is in the form of a hardened mass.

* * * * *